United States Patent [19]
Lehmbeck

[11] Patent Number: 5,968,774
[45] Date of Patent: Oct. 19, 1999

[54] HOST CELL EXPRESSING REDUCED LEVELS OF A METALLOPROTEASE AND METHODS USING THE HOST CELL IN PROTEIN PRODUCTION

[75] Inventor: Jan Lehmbeck, Veksø, Denmark

[73] Assignee: Novo Nordisk A/S, Bagsvaerd, Denmark

[21] Appl. No.: 09/207,844

[22] Filed: Dec. 8, 1998

Related U.S. Application Data

[62] Division of application No. 08/894,772, filed as application No. PCT/DK96/00111, Mar. 20, 1996, Pat. No. 5,861,280.

[30]     Foreign Application Priority Data

Mar. 20, 1995  [DK]  Denmark ................................. 0284/95

[51] Int. Cl.[6] ..................................................... C12P 21/02
[52] U.S. Cl. .................... 435/69.1; 435/69.4; 435/69.51; 435/69.6; 435/189; 435/198; 435/212; 435/484
[58] Field of Search ................................. 435/69.1, 69.4, 435/69.51, 69.6, 189, 198, 212, 484

[56]     References Cited

FOREIGN PATENT DOCUMENTS

| | | |
|---|---|---|
| 0 327 797 | 8/1989 | European Pat. Off. . |
| 0 341 215 | 11/1989 | European Pat. Off. . |
| WO 90/00192 | 1/1990 | WIPO . |
| WO 92/17595 | 10/1992 | WIPO . |
| WO 93/00925 | 1/1993 | WIPO . |

OTHER PUBLICATIONS

Tatsumi et al., "Cloning And Expression In Yeast Of A cDNA Clone Encoding *Aspergillus oryzae* Neutral Protease II, A Unique Metalloprotease", Mol Gen Genet, 1991, 228: pp. 97–103.

*Primary Examiner*—James Ketter
*Attorney, Agent, or Firm*—Steve T. Zelson, Esq.; Elias J. Lambiris, Esq.

[57]     ABSTRACT

The present invention relates to novel host cells and to methods of producing proteins. More specifically the invention relates to a host cell useful for the expression of heterologous proteins, which host cell has been genetically modified in order to express significantly reduced levels of a metalloprotease. Moreover the invention relates to a method of producing a heterologous protein, which method comprises cultivating the host cell in a suitable growth medium, followed by recovery of the desired protein.

40 Claims, 6 Drawing Sheets

5,968,774

HOST CELL EXPRESSING REDUCED LEVELS OF A METALLOPROTEASE AND METHODS USING THE HOST CELL IN PROTEIN PRODUCTION

CROSS-REFERENCE TO RELATED APPLICATIONS

This application is a divisional of U.S. application Ser. No. 08/894,772, filed Aug. 27, 1997, now U.S. Pat. No. 5,861,280, which is a 35 U.S.C. 371 national application of PCT/DK96/00111 filed Mar. 20, 1996 and claims priority under 35 U.S.C. 119 of Danish application 0284/95 filed Mar. 20, 1995, the contents of which are fully incorporated herein by reference.

TECHNICAL FIELD

The present invention relates to novel host cells and to methods of producing proteins. More specifically the invention relates to a host cell useful for the expression of heterologous proteins, which host cell has been genetically modified in order to express significantly reduced levels of a metalloprotease. Moreover the invention relates to a method of producing a heterologous protein, which method comprises cultivating the host cell in a suitable growth medium, followed by recovery of the desired protein.

BACKGROUND ART

The use of recombinant host cells in the expression of heterologous proteins has in recent years greatly simplified the production of large quantities of commercially valuable proteins, which otherwise are obtainable only by purification from their native sources. Currently, there is a varied selection of expression systems from which to choose for the production of any given protein, including eubacterial and eucaryotic hosts. The selection of an appropriate expression system often not only depends on the ability of the host cell to produce adequate yields of the protein in an active state, but also to a large extent may be governed by the intended end use of the protein.

One problem frequently encountered is the high level of proteolytic enzymes produced by a given host cell or in the culture medium. It has been suggested that one could provide host organism deprived of the ability of producing specific proteolytic compounds. For example, International Patent Application WO 90/00192 describes filamentous fungal hosts incapable of excreting enzymatically active aspartic proteinase, and EP 574 347 describes Aspergillus hosts defective in a serine protease of the subtilisin-type.

Metalloproteases have been isolated from a number of eucaryotic sources. Neutral metalloproteases, i.e. metalloproteases having optimal activity at neutral pH, isolated from strains of Aspergillus also have been reported. Neutral metalloproteases have been classified into two groups, NpI and NpII [Sekine; Agric. Biol. Chem. 1972 36 207–216]. Recently the nucleotide sequence of a neutral metalloprotease II cDNA from *Aspergillus oryzae* have been disclosed [Tatsumi H, Murakami S, Tsuji R F, Ishida Y, Murakami K, Masaki A, Kawabe H, Arimura H, Nakano E and Motai H; Mol. Gen. Genet. 1991 228 97–103]. The nucleotide sequence of a neutral metalloprotease I cDNA from *Aspergillus oryzae* have never been disclosed.

Although metalloproteases have been reported, their role in relation to reducing the stability of the products obtained from these organisms have never been described.

SUMMARY OF THE INVENTION

According to the present invention it has now been found that metalloproteases may reduce significantly the stability of the product obtained by a cell.

Accordingly, the present invention provides a host cell useful for the expression of a heterologous protein product, which cell has been genetically modified in order to express significantly reduced levels of a metalloprotease, as compared to the parental cell.

In another aspect, the invention provides a method of producing a heterologous protein product in a host cell of the invention, which method comprises introducing into the host cell a nucleic acid sequence encoding the protein, cultivating the host cell in a suitable growth medium, and isolating the heterologous protein product.

By the method of the invention, the proteolytic action arising from metalloproteases have been significantly reduced, thereby improving the stability of the protein obtained by the method. Moreover, the protein obtained by the method of the invention can be obtained as a precursor protein, i.e. a zymogen, a hybrid protein, a protein obtained as a pro sequence or pre-pro sequence, or in unmaturated form.

BRIEF DESCRIPTION OF THE DRAWINGS

The present invention is further illustrated by reference to the accompanying drawing, in which.

DETAILED DISCLOSURE OF THE INVENTION

Host Cells

Figure 1:
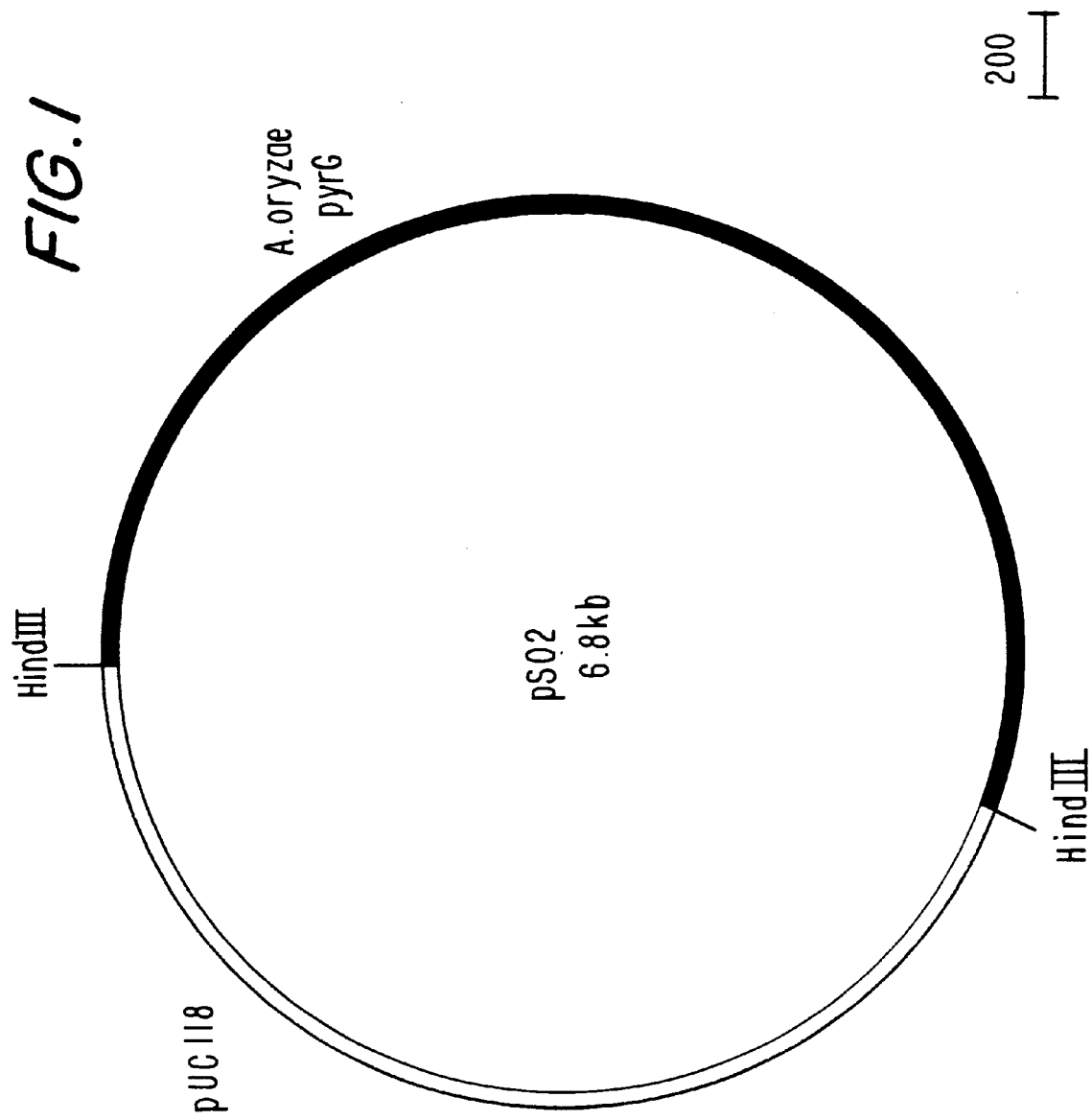
FIG. 1 shows a map of plasmid pSO2, cf. Example 2.

The present invention provides a host cell useful for the expression of heterologous proteins, which cell, when compared to the parental cell, has been genetically modified in order to express significantly reduced levels of a metalloprotease.

The parental cell is the source of said host cell. It may be a wild-type cell. Alternatively, besides a decrease in metalloprotease level, it may be genetically altered in another respect.

In order to produce the desired protein, the host cell of the invention obviously must hold structural (i.e. regions comprising the coding nucleotide sequences) and regulatory (i.e. regions comprising nucleotide sequences necessary for e.g. transcription, translation and termination) genetic regions necessary for the expression of the desired product. The nature of such structural and regulatory regions greatly depends on the product and the host cell in question. The genetic design of the host cell of the invention may be accomplished by the person skilled in the art, using standard recombinant DNA technology for the transformation or transfection of a host cell [vide e.g. Sambrook et al.; Molecular Cloning,. Cold Spring Harbor, N.Y., 1989].

Preferably, the host cell is modified by methods known in the art for introduction of an appropriate cloning vehicle, i.e. a plasmid or a vector, comprising a DNA fragment encoding the desired product. The cloning vehicle may be introduced into the host cell either as an autonomously replicating plasmid or integrated into the chromosome. Preferably the cloning vehicle comprises one or more structural regions operably linked to one or more appropriate regulatory regions.

The structural regions are regions holding nucleotide sequences encoding the desired product. The regulatory regions include promoter regions comprising transcription and translation control sequences, terminator regions comprising stop signals, and polyadenylation regions. The promoter, i.e. a nucleotide sequence exhibiting a transcriptional activity in the host cell of choice, may be one derived from a gene encoding an extracellular or an intracellular protein, preferably an enzyme, such as an amylase, a glucoamylase, a protease, a lipase, a cellulase, a xylanase, a oxidoreductase, a pectinase, a cutinase, or a glycolytic enzyme. Examples of suitable promoters for transcription in a fungal host cell are promoters derived from the gene encoding Aspergillus oryzae TAKA amylase, Aspergillus niger neutral α-amylase, Aspergillus niger acid stable α-amylase, Aspergillus niger or Aspergillus awamsii glucoamylase (gluA), Aspergillus niger acetamidase, Aspergillus oryzae alkaline protease, Aspergillus oryzae triose phosphatase isomerase, Rhizopus meihei aspartic proteinase, and Rhizopus meihei lipase. Preferred are the Aspergillus oryzae TAKA-amylase and Aspergillus awamsii gluA promoters.

The cloning vehicle may also comprise a selectable marker, e.g. a gene, the product of which complements a defect in the host cell, or one which confers antibiotic resistance, such as ampicillin, kanamycin, chloramphenicol or tetracycline resistance. Examples of Aspergillus selection markers include amdS, pyrG, argB, niaD and sC, a marker giving rise to hygromycin resistance. Preferred for use in an Aspergillus host cell are the amdS and pyrG markers of Aspergillus nidulans or Aspergillus oryzae. A frequently used mammalian marker is the dihydrofolate reductase (DHFR) gene. Furthermore, selection may be accomplished by co-transformation.

The procedures used to ligate the DNA construct of the invention, the promoter, terminator and other elements, respectively, and to insert them into suitable cloning vehicles containing the information necessary for replication, are well known to persons skilled in the art [vide e.g. Sambrook et al.; *Molecular Cloning*, Cold Spring Harbor, N.Y., 1989].

The host cell of the invention may be any host cell conventionally used for heterologous expression of proteins.

Preferably, the host cell of the invention is a yeast or a filamentous fungus capable of producing a desired protein. In particular, the yeast cell may be a strain of Saccharomyces, preferably *Saccharomyces cerevisiae*. In particular, the filamentous fungus may be a strain selected from the group consisting of Acremonium, Aspergillus, Candida, Cocliobolus, Endothia, Fusarium, Humicola, Neurospora, Rhizomucor, Rhizopus, Thermomyces, Trichoderma, Podospora, Pyricularia, or Penicillium.

In a preferred embodiment, the filamentous fungus is a strain selected from the group consisting of *Aspergillus oryzae, Aspergillus niger, Aspergillus nidulans, Aspergillus awamori, Aspergillus phoenicis, Aspergillus japonicus, Aspergillus foetus, Fusarium graminearum, Fusarium oxysporum, Fusarium solani, Humicola grisea, Neurospora crassa, Penicillium chrysogenum, Rhizomucor meihei, Trichoderma reesei*, or *Trichoderma viride*.

Products

The desired end product, i.e. the heterologous protein expressed by the host cell of the invention, may be any eubacterial or eucaryotic protein.

As defined herein, a "heterologous protein product" is a protein which is not native to the host cell, or a native protein in which modifications have been made to alter the native sequence, or a native protein whose expression is quantitatively altered as a result of a manipulation of a native regulatory sequence required for the expression of the native protein, such as a promoter, a ribosome binding site, etc., or other manipulation of the host cell by recombinant DNA techniques.

Owing to the absence of metalloprotease, the heterologous protein expressed by the host cell may also be a precursor protein, i.e. a zymogen, a hybrid protein, a protein obtained as a pro sequence or pre-pro sequence, or in unmaturated form. In a preferred embodiment the product is an enzyme.

In a more specific embodiment, the product is an eucaryotic enzyme, such as insulin, growth hormone, glucagon, somatostatin, interferon, PDGF, factor VII, factor VIII, urokinase, EPO, chymosin, tissue plasminogen activator, or serum albumin.

In another preferred embodiment, the product is an enzyme of fungal, of yeast, or of bacterial origin.

Preferably the enzyme is a glycosidase enzyme, e.g. an amylase, in particular an α-amylase (EC 3.2.1.1), a β-amylase (EC 3.2.1.2), a glucan 1,4-α-glucosidase (EC 3.2.1.3), a cellulase (EC 3.2.1.4), an endo-1,3(4)-β-glucanase (EC 3.2.1.6), an endo-1,4-β-glucanase (EC 3.2.1.8), a polygalacturonase (EC 3.2.1.15), an α-glucosidase (EC 3.2.1.20), a β-glucosidase (EC 3.2.1.21), an α-galactosidase (EC 3.2.1.22), a β-galactosidase (EC 3.2.1.23), a xylan-endo-1,3-β-xylosidase (EC 3.2.1.32), an endo-1,3-β-glucanase (EC 3.2.1.39), an endo-1,3-α-glucanase (EC 3.2.1.59), an endo-1,2-β-glucanase (EC 3.2.1.71), an endo-1,6-β-glucanase (EC 3.2.1.75), a cellulose-1,4-β-cellobiosidase (EC 3.2.1.91, also known as cellobiohydrolases).

In another preferred embodiment the enzyme is a lipolytic enzyme, in particular a lipase, an esterase, a phospholipase, or a lyso-phospholipase.

In a third preferred embodiment the enzyme is a phytase, in particular a 3-phytase (EC 3.1.3.8) or a 6-phytase (EC 3.1.3.26).

In a fourth preferred embodiment the enzyme is a proteolytic enzyme.

In a fifth preferred embodiment the enzyme is an oxidoreductase, such as a peroxidase or a laccase, a pectinase, or a cutinase.

Preferred hybrid polypeptides are prochymosin and pro-trypsin-like proteases.

Metalloproteases

In the context of this invention a metalloprotease is a proteolytic enzyme containing a catalytic zinc metal center which participates in the hydrolysis of the peptide backbone. The active zinc center differentiates these proteases from calpains, whose activities are dependent upon the presence of calcium. Confirmation of a protease as a metalloprotease is loss of proteolytic activity accomplished by removal of the zinc center. The zinc center can be removed with 1,10-phenanthroline (1 mM). After titration with $Zn^{2+}$ (0.1–100 $\mu$M), proteolytic activity is restored.

In a preferred embodiment, the metalloprotease contemplated in the context of this invention is a Fusarium metalloprotease, preferably a *Fusarium oxysporum* metalloprotease. In a most preferred embodiment, the metalloprotease is a *Fusarium oxysporum* p45 metalloprotease having the amino acid sequence presented as SEQ ID NO: 2, or a sequence homologous hereto.

In another preferred embodiment, the metalloprotease contemplated in the context of this invention is a neutral metalloprotease, which is a metalloprotease possessing optimal proteolytic activity in the neutral pH region, i.e. in the range of about pH 6–8, preferably the range of about pH 6.5–7.5, around pH 7.

More particularly, the metalloprotease contemplated in the context of this invention is a neutral Aspergillus metalloprotease of group NpI or NpII.

In a preferred embodiment, the metalloprotease is an *Aspergillus oryzae* Neutral Metalloprotease I (NpI) encoded by a cDNA comprising the partial nucleotide sequence presented as SEQ ID NO: 4, or a sequence homologous hereto.

The degree of homology may be determined as the degree of identity between the two sequences indicating a derivation of the first sequence from the second. The homology may suitably be determined by means of computer programs, by methods known in the art, e.g. by comparing 50 bp continuous sequences. As defined herein, the protein encoded by a homologous cDNA sequence exhibits a degree of homology of at least 70% homology, preferably more than 80% homology, more preferred more than 90% homology, most preferred more than 95% homology, with the sequence in question.

The gene encoding the metalloprotease may be identified by screening by hybridization for nucleic acid sequences coding for all of, or part of, the metalloprotease, e.g. by using synthetic oligonucleotide probes, that may be prepared on the basis of a cDNA sequence, e.g. the nucleotide sequences presented as SEQ ID NO: 1 and SEQ ID NO: 4, or on the basis of the amino acid sequence of the metalloprotease, in accordance with standard techniques [vide e.g. Sambrook et al.; *Molecular Cloning*, Cold Spring Harbor, N.Y., 1989].

Genetic Modifications

The host cell of the invention, genetically modified in order to express significantly reduced levels of a metalloprotease, may be modified using standard recombinant DNA technology, known to the person skilled in the art. The gene sequence responsible for the production of metalloprotease may be inactivated or eliminated entirely.

In a particular embodiment, the host cell of the invention is one genetically modified at the structural or regulatory regions encoding the metalloprotease. Known and useful techniques include, but are not limited to, specific or random mutagenesis, PCR generated mutagenesis, site specific DNA deletion, insertion and/or substitution, gene disruption or gene replacement techniques, anti-sense techniques, or a combination thereof.

Mutagenesis may be performed using a suitable physical or chemical mutagenizing agent. Examples of a physical or chemical mutagenizing agent suitable for the present purpose includes ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulfite, formic acid, and nucleotide analogues. When such agents are used, the mutagenesis is typically performed by incubating the cell to be mutagenized in the presence of the mutagenizing agent of choice under suitable conditions for the mutagenesis to take place, and selecting for mutated cells having a significantly reduced production of metalloprotease.

Modification may also be accomplished by introduction, substitution or removal of one or more nucleotides in the metalloprotease encoding sequence or a regulatory element required for the transcription or translation thereof. Nucleotides may, e.g., be inserted or removed so as to result in the introduction of a stop codon, the removal of the start codon or a change of the open reading frame. The modification or inactivation of the structural sequence or a regulatory element may be accomplished by site-directed mutagenesis or PCR generated mutagenesis in accordance with methods known in the art. Although in principle, the modification may be performed in vivo, i.e. directly on the cell carrying the metalloprotease gene, it is presently preferred to conduct the modification in vitro.

A convenient way to inactivate or reduce the metalloprotease production of a host cell of choice is based on the principles of gene interruption. This method involves the use of a DNA sequence corresponding to the endogenous gene or gene fragment which it is desired to destroy. Said DNA sequence is in vitro mutated to a defective gene and transformed into the host cell. By homologous recombination, the defective gene replaces the endogenous gene or gene fragment. It may be desirable that the defective gene or gene fragment encodes a marker which may be used for selection of transformants in which gene encoding the metalloprotease has been modified or destroyed.

Alternatively, the modification or inactivation of the DNA sequence may be performed by use of established anti-sense techniques using a nucleotide sequence complementary to the metalloprotease encoding sequence, e.g. the nucleotide sequences presented as SEQ ID NO: 1 and SEQ ID NO: 4.

Owing to genetic modification, the host cell of the invention expresses significantly reduced levels of metalloproteases. In a preferred embodiment the level of metalloprotease expressed by the host cell is reduced more than about 50%, preferably more than about 85%, more preferred more than about 90%, most preferred more than about 95%. In a most preferred embodiment, the product expressed by the host cell is essentially free of any metalloprotease activity.

Methods of Producing Proteins

In another aspect, the invention provides a method of producing proteins (i.e. polypeptides and/or proteins), which method comprises cultivating the host cell of the invention in a suitable growth medium, followed by recovery of the desired product.

By the method of the invention, the proteolytic action of metalloproteases have been significantly reduced, thereby improving the stability of the product obtained. Moreover, owing to the absence of metalloprotease, the heterologous protein expressed by the host cell may be obtained as a precursor protein, i.e. a zymogen, a hybrid protein, a protein obtained as a pro sequence or pre-pro sequence, or in unmaturated form.

The broth or medium used for culturing may be any conventional medium suitable for growing the host cell in question, and may be composed according to the principles of the prior art. The medium preferably contain carbon and nitrogen sources and other inorganic salts. Suitable media, e.g. minimal or complex media, are available from commercial suppliers, or may be prepared according to published receipts, e.g. the American Type Culture Collection (ATCC) Catalogue of strains.

After cultivation, the protein is recovered by conventional method for isolation and purification proteins from a culture broth. Well-known purification procedures include separating the cells from the medium by centrifugation or filtration, precipitating proteinaceous components of the medium by means of a salt such as ammonium sulphate, and chromatographic methods such as e.g. ion exchange chromatography, gel filtration chromatography, affinity chromatography, etc.

EXAMPLES

The invention is further illustrated with reference to the following examples which are not intended to be in any way limiting to the scope of the invention as claimed.

Materials and Methods
Strains
Aspergillus oryzae IFO 4177, available from Institute for Fermentation, Osaka, 17–25 Juso Hammachi 2-Chome Yodogawa-Ku, Osaka, Japan.

Fusarium oxysporum DSM 2672, deposited according to the Budapest Treaty on the International Recognition of the Deposit of Microorganisms for the Purposes of Patent Procedure at Deutsche Sammlung von Mikroorganismen und Zellkulturen GmbH (DSM), Mascheroder Weg 1b, DE-3300 Braunschweig, Germany, on Jun. 6, 1983.

Escherichia coli DH5α, Hanahan D, J. Mol. Biol. 1983 166 557.

Genes
NpI, which gene encodes Neutral Metalloprotease I.
NpII, which gene encodes Neutral Metalloprotease II.
pyrG: which gene encodes orotidine-5'-phosphate decarboxylase, an enzyme involved in the biosynthesis of uridine.

Plasmids
pUC118; Yanish-Perron et al., 1985 Gene 33 103.
pJaL389; Construction of this plasmid from cosmid 3E8 is described in Example 1.
pSO2; Construction of this plasmid is described in Example 2.
pJers4; A subclone of pSO2.
pJaL335; Construction of this plasmid from pSO2 is described in Example 2.
pSO5; Construction of this plasmid from pSO2 is described in Example 2.
pJaL198; Construction of this plasmid from pJaL198 is described in Example 3.
pJaL218; Construction of this plasmid from pJaL218 is described in Example 4.
p3SR2; Kelly J M and Hynes M J, EMBO Journal 1985 4 475–479.
pToC90; A subclone of p3SR2.
pToC56; Construction of this plasmid is described in EP 238,023 B.
pToC65; Construction of this plasmid is described in EP 531 372 B.
pCR™II; Available from Invitrogen Corporation, San Diego, Calif., USA.

Example 1
Cloning of Aspergillus oryzae Neutral Metalloprotease I (NpI)
Construction of a Cosmid Library of Aspergillus oryzae The library was essentially constructed according to the instruction from the supplier (Stratagene) of the "SuperCos1 Cosmid Vector Kit".

Genomic DNA of Aspergillus oryzae IFO 4177 was prepared from protoplasts made by standard procedures [cf. e.g. Christensen et al., Biotechnology 1989 6 1419–1422]. After isolation of the protoplasts these were pelleted by centrifugation at 2500 rpm for 5 minutes in a Labofuge™ T (Heto), the pellet was suspended in 10 mM NaCl, 20 mM Tris-HCl (pH 8.0), 1 mM EDTA, 100 μg/ml Proteinase™ K and 0.5% SDS, as described in the manual from the Supercos 1 Cosmid Vector Kit, as was the rest of the DNA preparations.

The size of the genomic DNA was analyzed by electrophoresis using the CHEF-gel apparatus from Biorad. A 1% agarose gel was run for 20 hours at 200 volt with a 10–50 second pulse. The gel was stained by ethidium bromide and photographed. The DNA was 50–100 kb in size. The DNA was partially restricted by Sau3A. The size of the restricted DNA was 20–50 kb determined the same way.

The CsCl gradient banded SuperCos1 vector was prepared according to the supplier's manual, as was ligation and packaging. After titration of the library, all of the packaging mix from one ligation and packaging was transfected into the host cells XL1-Blue MR and plated on 50 μg/ml ampicillin LB plates. Approx. 3800 colonies were obtained. Cosmid preparation from 10 colonies showed that they all had inserts of expected size. The colonies were picked individually and inoculated in microtiter plate wells with 100 μLB (100 μg/ml ampicillin) and incubated at 37° C. over night. 100 μl of 50% glycerol was added to each well, and the whole library was frozen at −80° C. A total of 3822 colonies were stored. This represents the Aspergillus oryzae genome approx. 4.4 times.

Cloning Fusarium oxysporum p45 Metalloprotease Gene
Purification

Fusarium oxysporum DSM 2672 broth is centrifuged at 9000 rpm for 10 minutes and the supernatant is filtered through a 0.45 μm filter. 200 ml of filtrate is concentrated down to 10 ml on an Amicon cell (PM 10 membrane) and Centriprep-0 (Amicon). 5 ml of concentrate is diluted to 100 ml and pH adjusted to 5 with acetic acid and run on a 1 ml Mono-S column in the following buffer: 0.1 M borate, 10 mM DMG, 2 mM calcium chloride, pH 5.2, in a gradient of 0 to 0.5 M sodium chloride over 70 minutes. After 10 minutes of wash in the above identified buffer at a flow rate of 1 ml/minute, 1.5 ml fractions are collected and concentrated on Centricon-10 (Amicon).

Gel filtration using Superose-12 (HR 10/30, Pharmacia) is performed in 0.1 M borate, 10 mM DMG, 2 mM $CaCl_2$, pH 6.5, flow rate 0.4 ml/minute. 0.4 ml fractions are collected. 200 μl samples are injected.

Proteolytic Enzyme Assay

Metalloprotease activity is measured as released trypsin activity from the pro-trypsin-like protease from the strain Fusarium oxysporum DSM 2672, after a 30–60 minutes pre-incubation at 25° C. in 0.1 M TRIS, 2 mM $CaCl_2$, pH 7 (at lower pH, 100 mM borate, 10 mM DMG, 2 mM $CaCl_2$ is used). The tryptic activity is measured in microtiter plates, 100 μl samples are mixed with 100 μl of substrate (stock: 87 mg/ml L-BAPNA (Sigma) in DMSO, diluted 50-fold in buffer), and the absorption at 405 nm is measured using a Thermomax reader from Molecular Devices.

SDS-PAGE and Electro Blotting onto PVDF

SDS-PAGE (10–27%, Novex) is run according to the manufacturer's instructions. Samples to be run are pre-incubated with PMSF before adding sample buffer. Electro blotting onto pro-blot membranes (Applied Biosystems) is performed in 3 mM $Na_2CO_3$, 10 mM $NaHCO_3$, 20% MeOH, pH 9.9, at 30 V for 2 hours using the blotting module from Novex. The pro-blot is stained as described by Applied Biosystems.

IEF-overlay

Isoelectric focusing (IEF) is run on an Ampholine PAG-plate (Pharmacia), pH 3.5 to 9.5, and stained according to the manufacturer's instructions. The gel to be overlaid is first equilibrated for 15 minutes in 0.1 M TRIS, 2 mM $CaCl_2$, pH 8.1, and then overlaid with 10 ml 1% agarose, 0.1 M TRIS, 2 mM $CaCl_2$, pH 8.1, added 300 μl L-BAPNA (Sigma) stock and 500 μl pro-trypsin-like Fusarium oxysporum DSM 2672 protease (~0.25 mg/ml).

Amino Acid Analysis and Amino Acid Sequencing

Microwave facilitated vapor phase hydrolysis of lyophilized samples is performed using the MDS-2000 hydrolysis station (CEM). 6 N HCl containing 1% phenol (scavenger) is used for creating the vapor phase. Hydrolysis time is 20 minutes at 70 psi (~148° C.). Hydrolysed samples are lyophilized and redissolved in 20 μl of 500 pmol/μl sarcosine and norvaline as internal standard. The analysis is done using the AminoQuant from Hewlett-Packard according to the manufacturer's instructions. 1 μl of sample is injected. Amino acid sequencing is performed using the 476A Protein Sequencer from Applied Biosystems according to the manufacturer's instructions. Premixed buffers are used for the online-HPLC.

Purification of p45 from *Fusarium oxysporum* Broth

The p45 metalloprotease is purified from concentrated and filtered fermentation broth by cation-exchange chromatography (Mono-S) followed by gel filtration on Superose 12. Fractions from Mono-S are selected by assaying for metalloprotease activity as released trypsin-like activity from pro-trypsin-like *Fusarium oxysporum* DSM 2672 protease.

Metalloprotease containing fractions from the Superose-12 column are identified by the same assay procedure as for the Mono-S fractions. The purified metalloprotease appears as a single band on SDS-PAGE at 45 kDa. Two isoforms of the metalloprotease are observed in IEF (pH 3.5–9.5) at respectively pI 8.4 and 8.7.

Results from amino acid analysis indicate that this metalloprotease (p45) has the N-terminal amino acid sequence shown in the Sequence Listing as SEQ ID NO: 3.

Cloning of *Fusarium oxysporum* p45 Metalloprotease Gene and Characterization of Recombinant p45

A portion of the *Fusarium oxysporum* p45 metalloproteasa gene is first cloned by PCR. One primer is designed using the N-terminal protein sequence (SEQ ID NO: 3), and a reverse primer is designed from an internal metalloprotease peptide sequence (residues 483–515 of SEQ ID NO: 1). PCR is performed using the DNA primers and genomic DNA isolated from *Fusarium oxysporum*. Genomic DNA is isolated as follows.

Approximately 15 g wet weight *Fusarium oxysporum* is grown in MY50 medium (50 g/l maltodextrin, 2 g/l $Mg_2SO_4$, 10 g/l $KH_2PO_4$, 2 g/l citric acid, 10 g/l yeast extract, 2 g/l urea, 2 g/l $KS_2SO_4$, 0.5 ml trace metal solution, adjusted to pH 6 with 5 N NaOH) at 30° C. Mycelia are suspended in 16 ml TE (10 mM TRIS, 1 mM EDTA, pH 8.0), split into two tubes, and approx. 12 g of 0.45–0.52 mm glass beads (Thomas Scientific) are added to each tube. The samples are alternately vortexed and iced for 30 second intervals until a noticeable viscosity breakdown occurs. The samples are alternately vortexed two additional 30 second intervals. 2.5 ml 20% SDS is added to each sample. The samples are mixed by inversion, incubated 10 minutes at room temperature, and mixed again. Samples are spun 8 minutes at 3.5 K at room temperature. Supernatants are combined in a 50 ml polypropylene tube. The sample is extracted with an equal volume of TE equilibrated with phenol:chloroform:isoamyl alcohol (25:24:1) (P/C/I extracted), then centrifuged 10 minutes at 10,000 rpm at 4° C. The supernatant is treated with 300 μl 10 mg/ml Proteinase K for 30 minutes at 25° C. The DNA is P/C/I extracted as described above, ethanol precipitated and dissolved in 5 ml TE. The sample is treated with 150 μl 10 mg/l RNAase A for 15 minutes at 65° C., then 15 minutes at 25° C. The sample is treated again with Proteinase K (100 μl 10 mg/ml for 1.5 hours at 25° C. and P/C/I extracted twice and ethanol precipitated. The DNA is pooled onto a bent pasteur pipet and transferred to 5 ml 80% ethanol. The sample is spun 3 minutes at 10,000 rpm. The DNA pellet is dried briefly, then dissolved in 1 ml TE.

PCR is used to clone a portion of the *Fusarium oxysporum* p45 gene. 50–100 ng *Fusarium oxysporum* genomic DNA is mixed with approx. 100 pmoles each of the synthetic PCR primer DNAs in 1X Taq buffer (Boehringer Mannheim) and a concentration of 100 μl each of dGTP, dATP, dTTP and dCTP in a volume of 50 μl. Taq DNA polymerase (Boehringer Mannheim), 1–5 units, is added, and the PCR incubations are, 95° C. for 5 minutes, then 35 cycles of [95° C. for 30 seconds; 50° C. for 1 minute; and 72° C. for 1 minute].

The PCR reaction produces two DNA fragments of approx. 1.0 and 1.3 kb in length. These fragments are isolated by gel electrophoresis, purified, cloned into an *E. coli* replicating plasmid, and sequenced using standard methods known in the art of molecular biology. The 1.0 kb DNA fragment is found to contain *Fusarium oxysporum* p45 gene sequences by a comparison of the translations of the DNA with amino acid sequences obtained from direct protein sequencing. Therefore, this 1.0 kb PCR generated DNA fragment is used as a probe to clone the entire metalloprotease gene from a *Fusarium oxysporum* genomic DNA library.

A genomic library in lambda phage is prepared from the *Fusarium oxysporum* genomic DNA using methods such as those described by Sambrook et al. [Sambrook et al.; *Molecular Cloning*, Cold Spring Harbor, N.Y., 1989]. A total of 50 μg genomic DNA is digested in a volume of 200 μl containing 10 mM TRIS, pH 7.5, 50 mM NaCl, 7 mM $MgCl_2$, 7 mM 2-mercaptoethanol, and 4 units restriction enzyme Sau3A for one minute at 25° C. Partially digested DNA of molecular size 10–20 kb is isolated by agarose gel electrophoresis, followed by electroelution into dialysis membrane and concentration using an Elutip-D column (Schleicher and Schuell). One μg of lambda arms of phage of EMBL4, that had been cut with restriction enzyme BamH1 and treated with phosphatase (Clonetech), is ligated with 300–400 μg Sau3A cut genomic DNA in a volume of 25 μl under standard conditions [cf. Sambrook et al.; *Molecular Cloning*, Cold Spring Harbor, N.Y., 1989]. Lambda phage are prepared from this litigation mix using a commercially available kit (Gigapack Gold II, Stratagene), following the manufacturers instructions. The plating of approx. 18,000 recombinant lambda phage, and the production of filter lifts (to N+ filters, Amersham) were performed using standard techniques [cf. Sambrook et al.; *Molecular Cloning*, Cold Spring Harbor, N.Y., 1989]. The filters are processed for hybridization with a Genious Kit for non-radioactive nucleic acids detection (Boehringer Mannheim) using the instructions provided by the manufacturer. The DNA used as p45 probe is the 1.0 kb PCR fragment obtained as described above. The probe is labelled by PCR incorporation of dioxigenin (DIG) using a DIG labelling kit and the instructions supplied by the manufacturer. Fifteen ng of the 1.0 kb p45 fragment is mixed in 1X Taq Buffer (Boehringer Mannheim) with 100 pmoles each N-terminal primer and internal reverse primer, and 1–5 units Taq polymerase (Boehringer Mannheim) in a total volume of 80 μl. Reaction conditions were 95° C. for 3 minutes, then 35 cycles of [95° C. for 30 seconds; 50° C. for 1 minute; and 72° C. for 1 minute], and 72° C. for 5 minutes. The filter hybridizations using the DIG labelled probe and the wash conditions were performed using the instructions provided by the Genious Kit manufacturer.

Hybridizing phages are detected with an alkaline phosphatase conjugated anti-dioxigenin antibody visualized with Lumiphos 530 as described by the manufacturer (Boehringer Mannheim). DNA preparations are made from the positive lambda clones using the Qiagen Lambda Midi Kit (QIAGEN, Inc.). DNA from one preparation is digested with restriction enzyme EcoR1 and a 6.3 kb fragment is subcloned into plasmid pUC118. DNA sequence analysis of portions of this subclone identified the entire coding region of the p45 gene, cf. SEQ ID NO: 1.

Cloning p45 Metalloprotease cDNA

Total RNA and poly-A RNA is prepared from *Fusarium oxysporum* according to the previous published protocols [Chirgwin et al., Biochemistry, 1988 18 5294–5299; Aviv and Leder, *Proc. Natl. Acad. Sci., USA*, 1972 69 1408–1412; Sambrook et al.; *Molecular Cloning*, Cold Spring Harbor, N.Y., 1989] with the following modifications.

Specifically, mycelia is ground in liquid nitrogen to a fine powder and then resuspended, with stirring, in a lysis buffer containing 4 M guanidinium thiocyanate, 0.5% Na-laurylsarcosine, 25 mM Na-citrate and 0.1 M 2-mercaptoethanol, pH 7.0, for 30 minutes at room temperature. Cell debris is removed by low speed (5000 rpm for 30 minutes) centrifugation. Typically, the poly-A RNA fraction is isolated using oligo (dT) cellulose obtained from Boehringer Mannheim.

The poly-A RNA is used to generate CDNA using the hairpin/RNaseH method [Sambrook et al.; *Molecular Cloning*, Cold Spring Harbor, N.Y., 1989]. Specifically, 5 µg poly-A RNA in 5 µl water is heated at 70° C., then placed on ice. A total reaction mix of 50 µl is prepared containing the poly-A RNA, 50 mM TRIS, pH 8.3, 75 mM KCl, 3 mM $MgCl_2$, 10 mM DTT, 1 mM each dGTP, dATP, dTTP and dCTP, 40 units RNasin, 10 µg oligo (dT12-18) primer, and 1000 units SuperScript II RNase H- reverse transcriptase (Bethesda Research Laboratories). The mix is incubated at 45° C. for one hour. Then 30 µl of 10 mM TRIS, pH 7.5, 1 mM EDTA, 40 µg glycogen carrier (Boehringer Mannheim), 0.2 volumes 10 M ammoniun acetate, and 2.5 volumes ethanol were added to precipitate the nucleic acids. After centrifugation, the pellet is resuspended in 20 mM TRIS, pH 7.4, 90 mM KCl, 4.6 mM $MgCl_2$, 10 mM ammonium sulphate, 16 µM $\beta NAD^+$, 100 µM each dGTP, dATP, dTTP and dCTP, 44 units *E. coli* DNA polymerase I, 6.25 units RNaseH, and 10.5 units DNA ligase. Second strand DNA synthesis is performed in this solution at 16° C. for 3 hours. The DNA is concentrated by ethanol precipitation and the pellet is resuspended in 30 µl of 30 mM Na-acetate, pH 4.6, 300 mM NaCl, 1 mM $ZnSO_4$, 0.35 mM DTT, 2% glycerol, and 30 units Mung Bean nuclease (Bethesda Research Laboratories) at 30° C. for 30 minutes. The DNA solution is neutralized with 70 µl 10 mM TRIS, pH 7.5, 1 mM EDTA, phenol extracted, and ethanol precipitated. The pellet is treated with 7.5 units T4 polymerase (Invitrogen) at 25° C. for 15 minutes in 50 µl buffer (20 mM TRIS-acetate, pH 7.9, 10 mM Mg-acetate, 50 mM K-acetate, 1 mM DTT, 0.5 mM each dGTP, dATP, dTTP and dCTP). The reaction is stopped by addition of EDTA to 20 mM followed by phenol extraction and ethanol precipitation. The result of this procedure is double stranded cDNA with blunt ends suitable for attachment of DNA linkers and cloning into any vector.

The cDNA with EcoR1 linkers is size fractionated on an agarose gel to obtain cDNAs of molecular size 0.7 kb or greater. The cDNA is recovered from the gel by electroelution and purified by phenol extraction and ethanol precipitation. The size fractionated cDNA is used to construct a lambda cDNA library.The cDNA is cloned into lambda ZIPLOX arms (Gibco BRL). Full length CDNA clones are identified using a 467 bp dioxigenin labeled fragment as probe (bp 336–803 of the genomic clone) with the techniques of plaque lifts and DNA hybridization as previously described. Full length cDNA is recovered in plasmid pZL1 as described by the manufacturer (strains and plasmid from Bibco BRL).

The full length cDNA is sequenced and compared with the sequence of the genomic DNA. The genomic DNA is 2052 bp in length and contains three introns. The predicted coding region of pre-pro p45 metalloprotease consists of a putative 18 amino acid signal sequence, a 226 amino acid pro-region, and a 388 amino acid mature region, as shown in SEQ ID NO: 1.

Preparation of *Fusarium oxysporum* p45 Metalloprotease Probe

A clone from the above cDNA library was selected and designated pDM115. Plasmid pDM115 contains a 1.76 kb fragment of *Fusarium oxysporum* cDNA, that encodes part of the p45 gene. This plasmid was digested with SalI and the fragments were separated on a 1% agarose gel. The 1.5 kb fragment was cut out and DNA eluted. This fragment was labelled with 32-P-dATP by random-primed labeling and used for either Southern or colony lift probing.

Screening *Aspergillus oryzae* Library with *Fusarium oxysporum* p45 Probe

The individually frozen colonies in the library were inoculated onto LB plates (100 µg/ml ampicillin) by using a multipin device with 6 times 8 pins fitting into half a microtiter dish. Plates were made containing colonies from all clones in the library. The plates were incubated at 37° C. over night. Sterilized Whatman 540 filters cut to the size of a petri dish were placed upon the colonies which were incubated for two more hours at 37° C. The filters were transferred to LB plates containing 200 µg/ml of chloramphenicol and the plates were incubated over night at 37° C. The next day the filters were washed twice in 0.5 M NaOH for 5 minutes, then twice in 0.5 M Tris-HCl (pH 7.4) for 5 minutes and then twice in 2× SSC for 5 minutes. The filters were wet with ethanol and air dried.

The filters were hybridized with the 1.5 kb $^{32}P$ labelled DNA fragment from pDM115 containing the protease gene from *Fusarium oxysporum*. The hybridization was carried out for 16 hours at 65° C. in 10× Denhart, 5× SSC, 0.02 M EDTA, 1% SDS, 0.15 mg/ml polyA, and 0.05 mg/ml yeast tRNA. After hybridization the filters were washed in 2× SSC, 0.1% SDS at 65° C. twice and placed on X-ray films. Three colonies showed hybridization to the probe, namely 3E8, 3C1 and 2A5, the names refer to their position in the library.

Characterization of the Cosmid Clones

By restriction analysis it was establised that two of the three cosmid clones (3E8 and 3C1) contained inserts which were derived from the same region of the *Aspergillus oryzae* genome.

3 µg of cosmid DNA was digested with EcoRI and fractionated by agarose gel electroferase. The DNA was transferred to Immobilan-N membrane filters and hybridized with the 1.5 kb radiolabelled probe from pDM115. The probe hybridized to a 4 kb EcoRI fragment in both cosmid clones. The 4.0 kb EcoRI fragment was chosen for further analysis.

Cloning of NpI into the Plasmid pToC65 and its Sequence

Plasmid pToC65 was digested with SacI and treated with bacterial alkaline phosphatase to remove the 5'-phosphate groups according to the manufacturers instructions. Afterwards it was phenol extracted and precipitated.

The 5.5 kb SacI fragment from cosmid clone 3E8 containing the *Aspergillus oryzae* NpI gene was isolated by gel electrophoresis and purified.

The two fragments were mixed together and ligated. After transformations of *E. coli*, the colonies carrying the correct plasmid were identified by restriction enzyme digestion of mini-plasmid preparations. This plasmid was called pJaL389.

Comparison of DNA sequence analysis of portions of this subclone to other known NpI gene sequences was used to identify that the subcdone contains the coding region of the *Aspergillus oryzae* NpI gene.

Example 2

Genomic Disrupton of *Aspergillus oryzae* Neutral Metalloprotease NpI

In order to generate strains of *Aspergillus oryzae* that are specifically deficient in the production of NpI, a gene replacement strategy as described by Miller et al.; *Mol. Cell. Biol.* 1985 5 1714–1721, was employed. Below, these experiments are described in more details.

Cloning of the *Aspergillus oryzae* pyrG gene

The *Aspergillus oryzae* pyrG gene was cloned by cross hybridization with the *Aspergillus niger* pyrG gene [W. van Hartingsveldt et al.; *Mol. Gen. Genet* 1987 206 71–75]. A lambda library of partial SauIIIA digested *Aspergillus oryzae* IFO 4177 DNA was probed at low stringency with a 1 kb DNA fragment from the *Aspergillus niger* pyrG gene. DNA from a positive clone was subcloned into a pUC118 vector. The resultant plasmid, pSO2, was shown to contain the pyrG gene by complementation of an *Aspergillus niger* pyrG - mutant, cf. FIG. 1.

Construction of an *Aspergillus oryzae* pyrG Minus Strain

A pyrG deletion plasmid, pSO5, containing about 1 kb of pyrG flanking sequences on each end, was constructed from the plasmid pSO2. The strain *Aspergillus oryzae* IFO 4177 was transformed with this construct and transformants were selected by resistance to 5-fluoro-orotic acid, a phenotype characteristic of pyrG mutants.

One transformant, HowB101, was shown by Southern analysis to have the expected deletion at the pyrG locus. Being a pyrG mutant, HowB101 requires uridine for growth. HowB101 can be transformed with the wt pyrG gene by selection for ability to grow without uridine.

Figure 2:
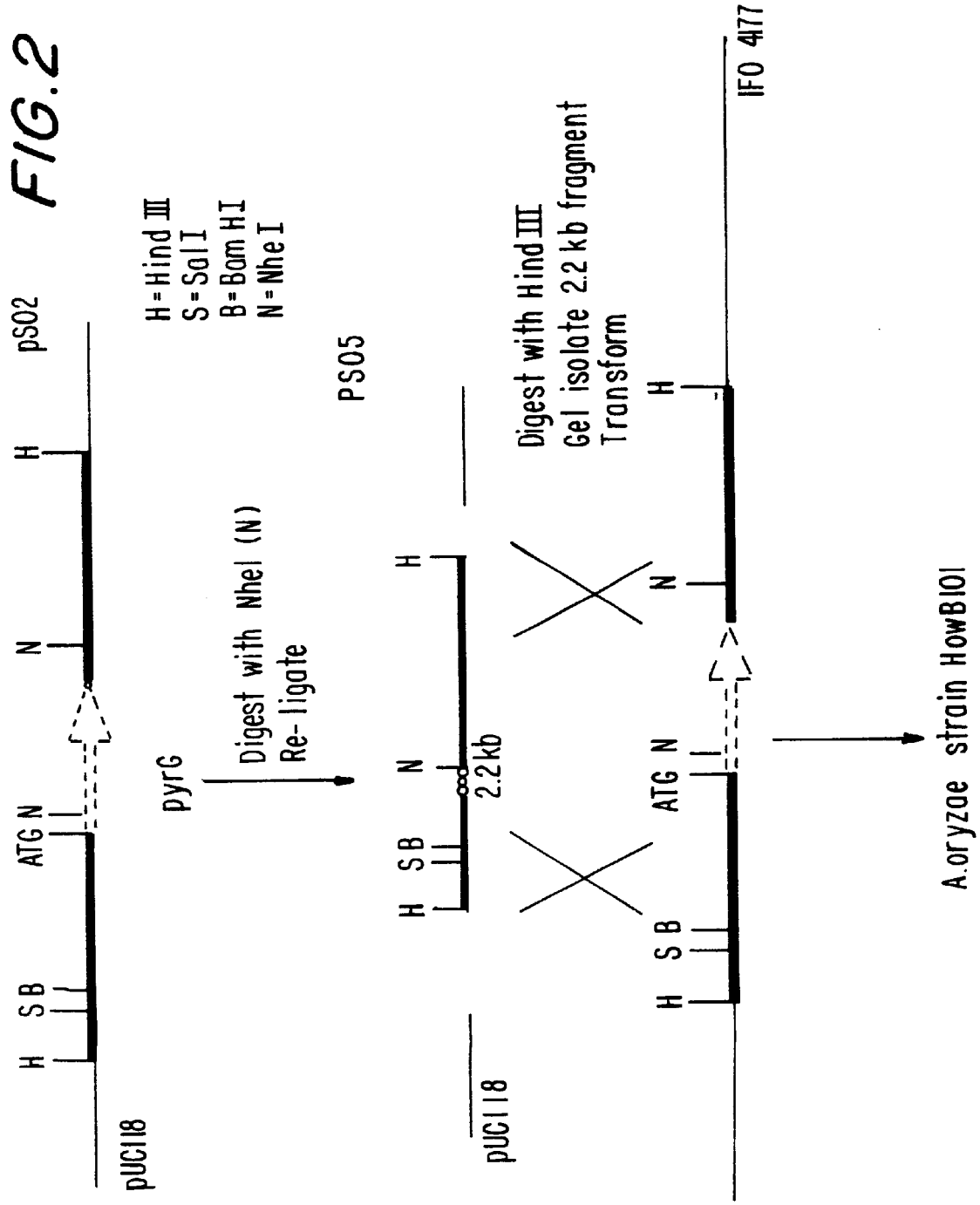
FIG. 2 shows the construction of *Aspergillus oryzae* strain HowB101, cf. Example 2.

The steps involved in the construction of HowB101 are illustrated in FIG. 2.

Construction of Plasmid pJaL335

In order to amplify a 431 bp fragment located 479 nucleotides upstream from the 5' end of the *Aspergillus oryzae* pyrG genet, the two following oligonucleotides were made: Primer A: GGAGGAAGATCT CTCTGGTACTCTTCGATCTC; SEQ ID NO: 5; and Primer B: GGAGGAGAATTCAAGCTT CTTCTACATCACAGTTTGAAAGC; SEQ ID NO: 6. The underlined part corresponds to the *Aspergillus oryzae* pyrG gene sequence.

The 5' ends of the primers were for facilitating cloning (Primer A contains a BgIII restriction endonuclease site, and primer B contains a EcoRI and a HindIII restriction endonuclase site).

Plasmid pSO2 was used as template in the PCR reaction. Amplification was performed in 100 μl volumes containing 2.5 units Taq-polymerase, 100 ng of pSO2, 50 mM KCl, 10 mM Tris-HCl pH 8.0, 1.5 mM MgCl$_2$, 250 nM of each dNTP, and 10 pmol of each of the two primers described above.

Figure 3:
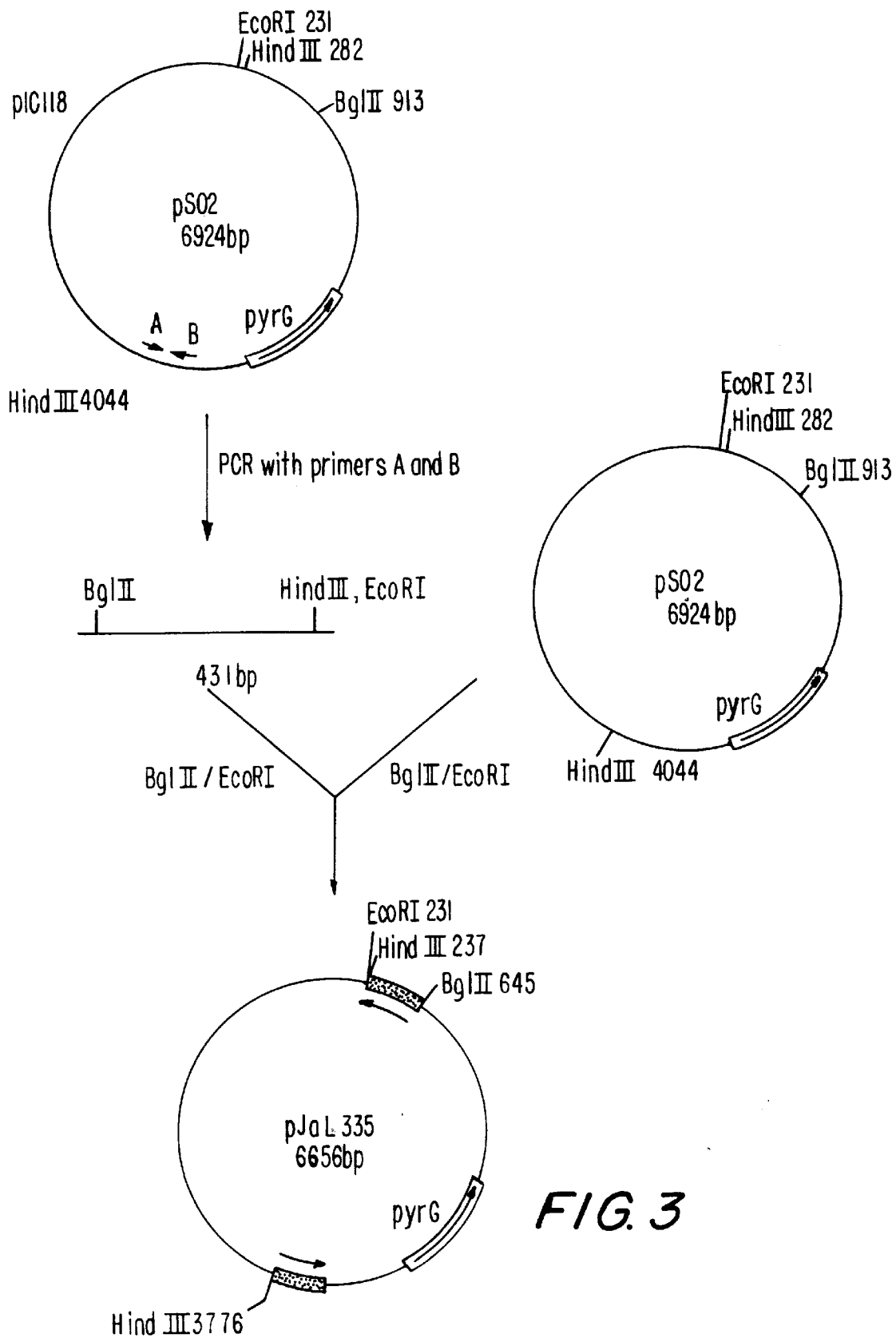
FIG. 3 shows the construction of plasmid pJaL335, cf. Example 2.

Amplification was carried out in a Perkin-Elmer Cetus DNA Termal 480, and consisted of one cycle of 3 minutes at 94° C., followed by 25 cycles of 1 minutes at 94° C., 30 seconds at 55° C., and 1 minutes at 72° C. The PCR reaction produced one DNA fragment of 430 bp in length. This fragment was digested with BgIII and EcoRI, and isolated by gel electrophoresis. It was purified and cloned into the corresponding site in plasmid pSO2. The resulting plasmid was called pJaL335. The construction of pJaL335 is illustrated in FIG. 3.

Construction of Disruption Plasmid pJaL399

Plasmid pJaL389 was digested with BaII, and treated with Klenow polymerase to make the ends blunt. The 7.1 kb fragment was isolated by gel electrophoresis, and purified. This DNA fragment was then treated with bacterial alkaline phosphatase to remove the 5' phosphate groups according to the manufacturer's instructions and phenol extracted and precipitated.

Plasmid pJaL335 was digested with HindIII, and treated with Klenow polymerase to make the ends blunt. The 3.5 kb fragment encoding the *Aspergillus oryzae* pyrG gene was isolated by gel electrophoresis and purified.

Figure 4:
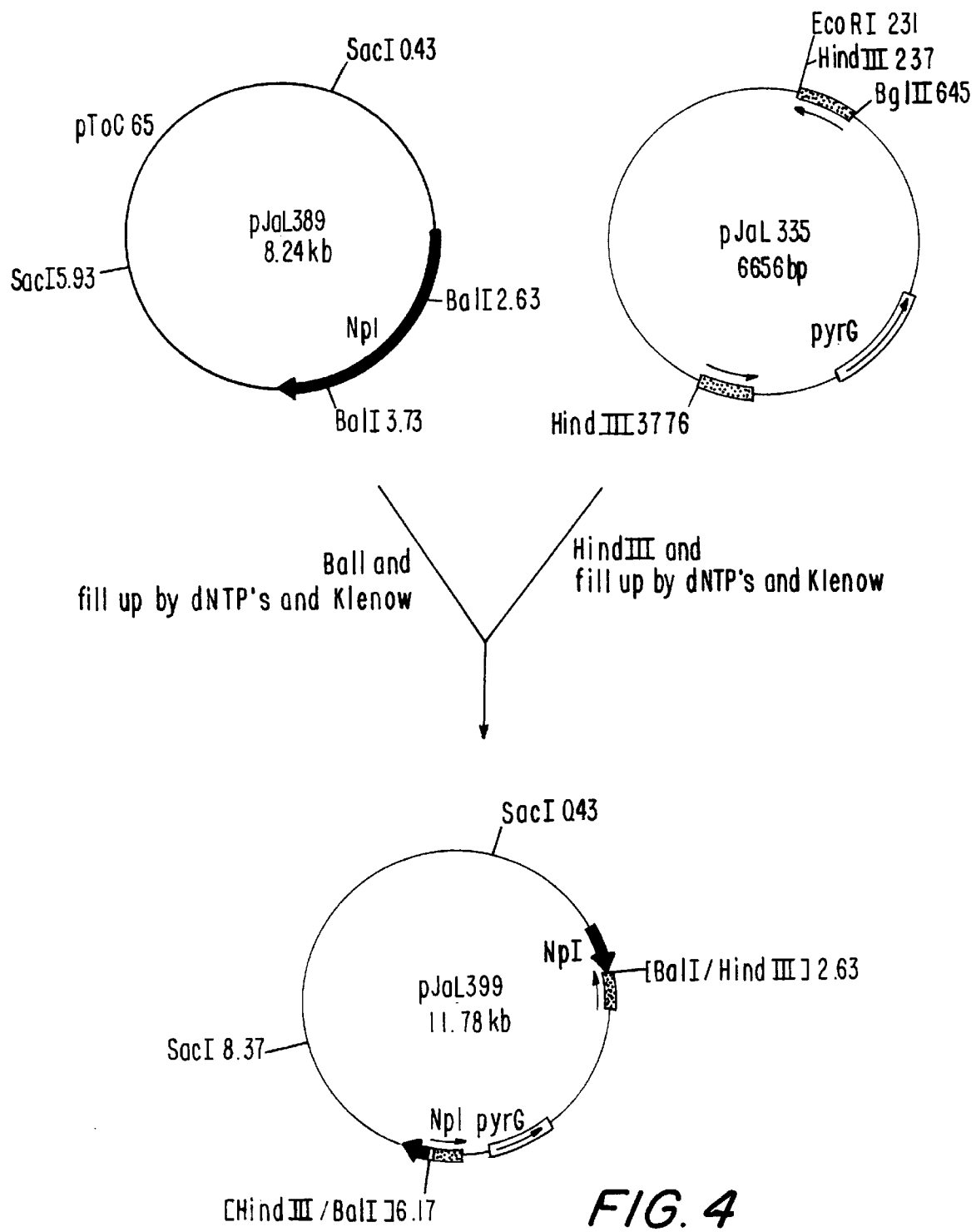
FIG. 4 shows the construction of plasmid pJaL399, cf. Example 2.

The two fragments were mixed together and ligated. After transformations of *E. coli*, the colonies carrying the correct plasmids were identified by restriction enzyme digestion of mini-plasmid preparations. The construction of pJaL399 is illustrated in FIG. 4.

pJaL399 holds a pToC65 vector containing a fragment which carries the NpI gene flanked by SacI sites, and where the central 1.1 kb BaII fragment has been replaced by an 3.5 kb DNA fragment encoding the *Aspergillus oryzae* pyrG gene.

Transformation of *Aspergillus oryzae*

15 μg of plasmid pJaL399 are digested to completion by SacI. The completeness of the digest is checked by running an aliquot on a gel and the remainder of the DNA is phenol extracted, precipitated and resuspended in 10 8,25 μl of sterile water.

The transformation of *Aspergillus oryzae* HowB101 host strain is preformed by the protoplast method [Christensen et al.; *Biotechnology* 1988 6 1419–1422]. Typically, *Aspergillus oryzae* mycelia is grown in a rich nutrient broth. The mycelia is separated from the broth by filtration. Novozymem™ (available from Novo Nordisk A/S, Denmark) is added to the mycelia in an osmotically stabilizing buffer such as 1.2 M MgSO$_4$ buffered to pH 5.0 with sodium phosphate. The suspension is incubated for 60 minutes at 37° C. with agitation. The protoplasts are filtered through mira-cloth to remove mycelial debris. The protoplasts are harvested and washed twice with STC (1.2 M sorbitol, 10 mM CaCl$_2$, 10 mM Tris-HCl pH 7.5). Finally, the protoplasts are resuspended in 200–1000 μl STC.

For transformation 5 μg DNA is added to 100 μl protoplast suspension. 200 μl PEG solution (60% PEG 4000, 10 mM CaCl$_2$, 10 mM Tris-HCl pH 7.5) was added, and the mixture is incubated for 20 minutes at room temperature. The protoplasts are harvested and washed twice with 1.2 M sorbitol. The protoplasts are finally resuspended in 200 μl 1.2 M sorbitol, plated on selective plates (minimal medium+ 10 g/l Bacto-Agar (Difco), and incubated at 37° C. After 3–4 days of growth at 37° C., stable transformants will appear as vigorously growing and sporulating colonies.

Identification of Gene Disruption

From the stable colonies, individual spores are streaked on fresh minimal plates. Single colonies are selected and restreaked to give pure cultures. These are used to inoculate 10 ml of liquid YPM medium (1% yeast extrat, 1% peptone, 2% maltose). After 18 hours at 30° C. and shaking at 180 rpm, the mycelia is harvested on filter paper. Mycelia is then transferred to an 2 ml eppendorf tube and freeze dried.

After freeze drying DNA is prepared from the individual mycelia by grinding the mycelia to a fine powder with a pestle in the tube. This powder is resuspended in 0.5 ml of 50 mM EDTA pH 8.0, 0.2% SDS, 1 μl DEP, by vortexing. After incubation at 65° C. for 20 minutes, 0.1 ml 5 M KAc pH 6.5, is added and the solution is mixed and incubated on ice for 5 minutes. The cell debris is separated from the DNA solution by centrifugation at 20.000 rpm for 5 minutes. 0.4 ml supernatant is precipitated with 0.3 ml isopropanol and centrifugated at 20.000 rpm for 10 minutes. The DNA pellet is redisolved in 100 μl of sterile TE buffer containing 0.1 mg/ml RNAaseA.

3 μg of each DNA is digested with BalI, fractionated by agarose gel electroferase, transferred to Immobilan-N membrane filters. The filters were hybridized with the 5.5 kb $^{32}$P labelled DNA SacI fragment from pJaL389 containing the NpI protease gene. Strains which carry a disruption of the NpI gene are recognized by lacking the 1.1 kb BalI hybridizing fragment as well as having altered mobility of the other two flanking fragments.

Example 3
Cloning of Aspergillus oryzae Neutral Metalloprotease II (NpII) Construction of pJaL198

From the published cDNA nucleotide sequence encoding Aspergillus oryzae NpII [Tatsumi et al.; Mol. Gen. Genet. 1991 228 97–103], two oligonuclotides were designed so that the encoding part of the NpII gene was amplified in a PCR reaction.

A primer (CTAGGATCCAAGGCATTT ATGCGTGTCACTACTCTC; SEQ ID NO: 7) was constructed so that the 3' end of the nucleotide sequence corresponds to the N-terminal part of the NpII gene (underlined), and the 5'-end is for facilitating cloning (contains a BamHI restriction endonuclease site).

A primer (CTACTCGAG TTAGCACTTGAGCTCGATAGC; SEQ ID NO: 8) was constructed so that the 3' end of the nucleotide sequence corresponds to the C-terminal part of the NpII gene (underlined), and the 5'-end is for facilitating cloning (contains a XhoI restriction endonuclease site).

Genomic DNA from Aspergillus oryzae IFO 4177 was used as template in the PCR reaction. Amplification reaction was performed in 100 μl volumes containing 2.5 units Taq-polymerase, 100 ng of Aspergillus oryzae genomic DNA, 50 mM KCl, 10 mM Tris-HCl pH 8.0, 1.5 mM MgCl$_2$, 250 nM of each dNTP, and 100 pM of each of the two primers described above.

Amplification was carried out in a Perkin-Elmer Cetus DNA Termal 480, and consisted of one cycle of 3 minutes at 94° C., followed by 25 cycles of 1 minutes at 94° C., 30 seconds at 55° C., and 1 minutes at 72° C. The PCR reaction produces one DNA fragment of approx. 1.1 kb in length. This fragment was isolated by gel electrophoresis, purified, cloned into the vector pCR™II (Invitrogen Corporation), and sequenced using standard methods known in the art of molecular biology. The resulting plasmid was called pJaL198.

Example 4
Genomic Disruption of NpII
Construction of JaL121

In order to generate strains of Aspergillus oryzae that were specifically deficient in the production of NpII, a gene replacement strategy as described by Miller et al.; Mol. Cell. Biol. 1985 5 1714–1721, was employed.

Cloning Aspergillus oryzae pyrG Gene

The Aspergillus oryzae pyrG gene was cloned by cross hybridization with the Aspergillus niger pyrG gene [W. van Hartingsveldt et al.; Mol. Gen. Genet. 1987 206 71–75]. A lambda library of partial SauIIIA digested Aspergillus oryzae IFO 4177 DNA was probed at low stringency with a 1 kb DNA fragment from the Aspergillus niger pyrG gene. DNA from a positive clone was subcloned into a pUC118 vector. The resultant plasmid, pSO2, was shown to contain the pyrG gene by complementation of an Aspergillus niger pyrG - mutant, cf. FIG. 1.

Construction of an Aspergillus oryzae pyrG Minus Strain

A pyrG deletion plasmid, pSO5, containing about 1 kb of pyrG flanking sequences on each end, was constructed from the plasmid pSO2. The strain Aspergillus oryzae IFO 4177 was transformed with this construct, and transformants were selected by resistance to 5-fluoro-orotic acid, a phenotype characteristic of pyrG mutants. One transformant, HowB101, was shown by Southern analysis to have the expected deletion at the pyrG locus. Being a pyrG mutant, HowB101requires uridine for growth. HowB101 can be transformed with the wt pyrG gene by selection for ability to grow without uridine.

The steps involved in the construction of HowB101 are illustrated in FIG. 2.

Construction of Disruption Plasmid pJaL218

Plasmid pJaL198 is digested with BstEII and treated with Klenow polymerase to make the ends blunt. The 4.9 kb fragment was isolated by gel electrophoresis and purified. This DNA fragment was then treated with bacterial alkaline phosphatase to remove the 5' phosphate groups, according to the manufacturers instructions, phenol extracted and precipitated.

Plasmid pJers4 was digested with HindIII and treated with Klenow polymerase to make the ends blunt. The 1.8 kb fragment encoding the Aspergillus oryzae pyrG gene was isolated by gel electrophoresis and purified.

Figure 5:
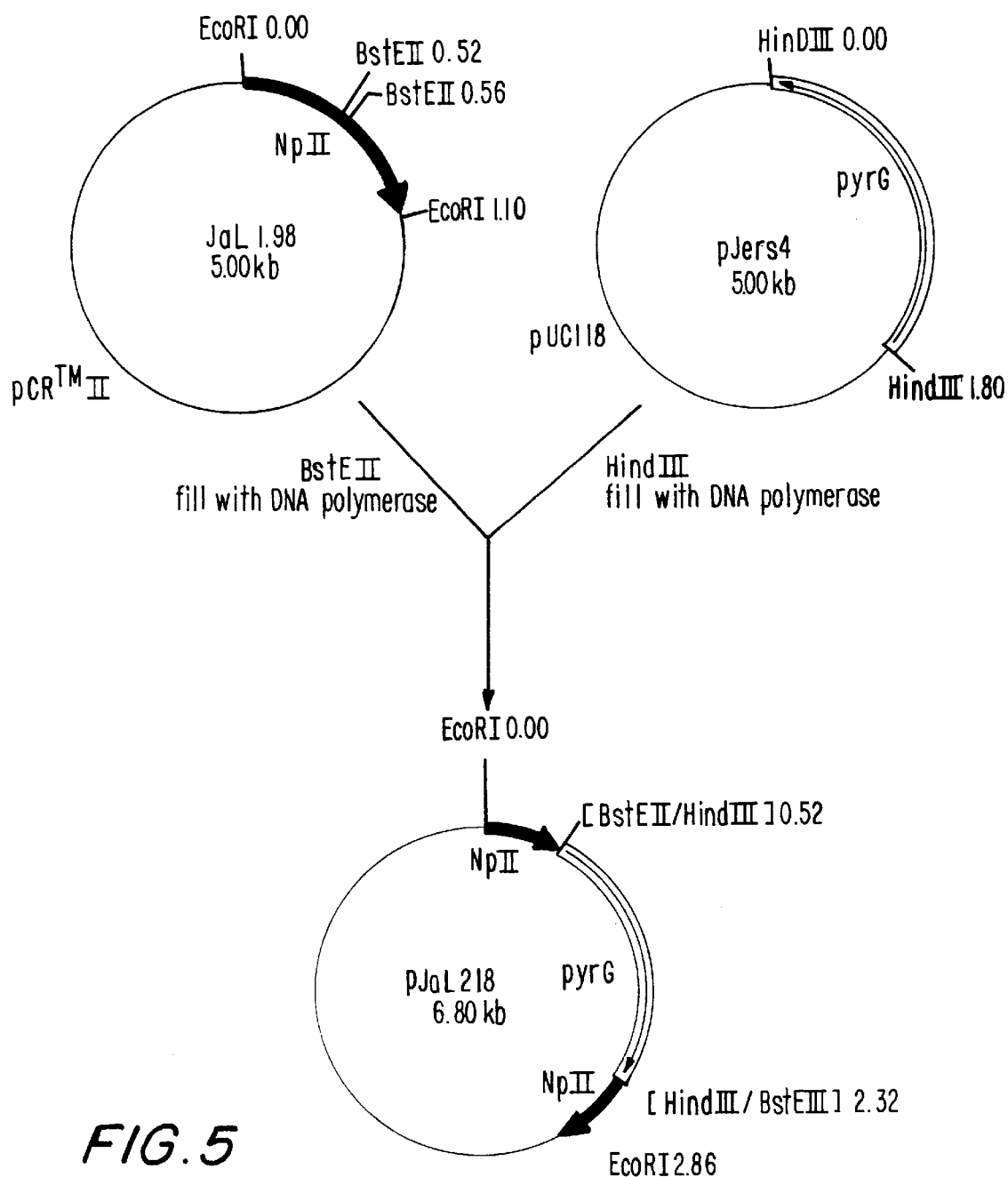
FIG. 5 shows the construction of plasmid pJaL218, cf. Example 4.

The two fragments were mixed and ligated. After transformations of E. coli DH5α, the colonies carrying the correct plasmids are identified by restriction enzyme digestion of mini-plasmid preparations. The construction of pJaL218 is illustrated in FIG. 5.

pJaL218 consists of the pCR™II vector containing a fragment which carries the NpII gene flanked by EcoRI sites, in which the central BstEII fragment has been replaced by a 1.8 kb DNA fragment encoding the Aspergillus oryzae pyrG gene.

Transformation Aspergillus oryzae

15 μg of plasmid pJaL218 is digested to completion by EcoRI. The completeness of the digest was checked by running an aliquot on a gel. The remainder of the DNA was phenol extracted, precipitated and resuspended in 10 μl of sterile water.

The transformation of Aspergillus oryzae HowB101 host strain was performed by the protoplast method [Christensen et al.; Biotechnology 1988 6 1419–1422]. Typically, Aspergillus oryzae mycelia was grown in a rich nutrient broth. The mycelia was separated from the broth by filtration. Novozyme™ (available from Novo Nordisk A/S, Denmark) was added to the mycelia in an osmotically stabilizing buffer, 1.2 M MgSO$_4$, sodium phosphate buffer pH 5.0. The suspension was incubated for 60 minutes at 37° C. with agitation. The protoplast was filtered through Miracloth to remove mycelial debris. The protoplast was harvested and washed twice with STC (1.2 M sorbitol, 10 mM CaCl$_2$, 10 mM Tris-HCl pH 7.5). The protoplast was finally resuspended in 200–1000 μl STC.

For transformation, 5 μg DNA was added to 100 μl protoplast suspension. 200 μl PEG solution (60% PEG 4000, 10 mM CaCl$_2$, 10 mM Tris-HCl pH 7.5) was added, and the mixture is incubated for 20 minutes at ambient temperature. The protoplast was harvested and washed twice with 1.2 M sorbitol. The protoplast was finally resuspended 200 μl 1.2

M sorbitol, plated on selective plates (minimal medium+10 g/l Bacto-Agar (Difco), and incubated at 37° C.

After 3–4 days of growth at 37° C., stable transformants appear as vigorously growing and sporulating colonies.
Identification of Gene Disruptions From stable colonies, individual spores are streaked on fresh minimal plates. Single colonies are selected and restreaked to give pure cultures.

Thirty-three transformants were screened to see if the transformed DNA fragment had integrated by a double overcross into the corresponding gene on the chromosome by PCR. PCR reaction and genomic DNA from the transformants was performed as described above.

The primers used were CCCTTCTTTCCAAACCG (SEQ ID NO: 9), which is located 5' from the encoding region of the NpII gene, and pyrG-5' (GGGTGAGCCACTGCCTC; SEQ ID NO: 10), which is specific for the pyrG gene. One transformant yielded the expected PCR product on 1.1 kb.

From Southern blots, where genomic DNA from the transformant and from *Aspergillus oryzae* was digested with EcoRI, fractionated by agarose gel electrophoresis, transferred to Immobilan-N membrane filters, and probed with the 1.1 kb EcoRI fragment from pJaL198 containing the NpII gene, it was found that the wild-type band on 3.8 kb was shifted to a 10 kb band in the transformant. This proves that the transformed DNA was integrated into the NpII gene in multiple copies. The strain was designated JaL121.

Example 5
Production of Chymosin in JaL121

Figure 6:
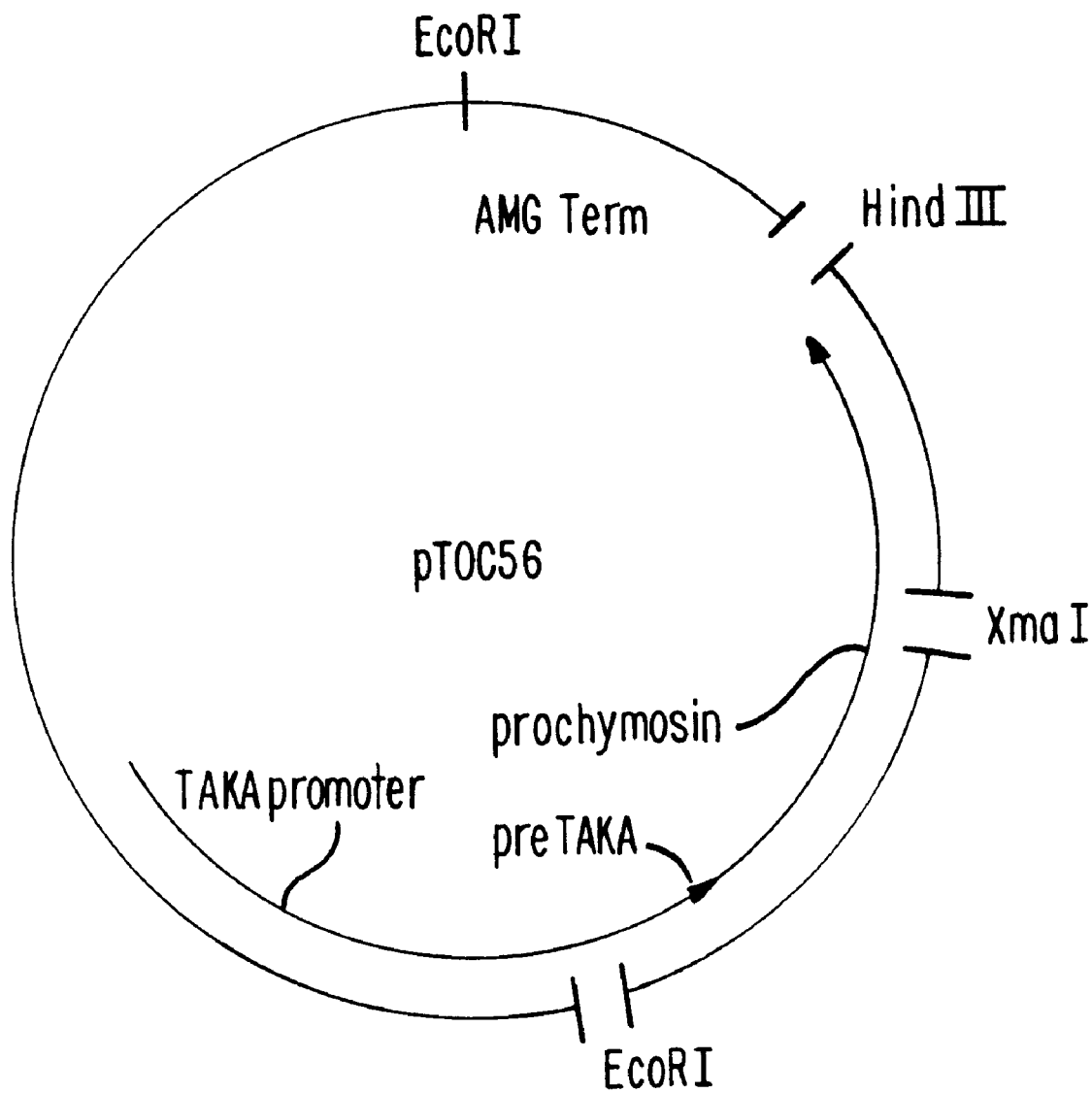
FIG. 6 shows a map of plasmid pToC56, cf. Example 5.

*Aspergillus oryzae* strain JaL121 was transformed with the plasmid pToC56 (cf. FIG. 6), which is a fungal expression plasmid for the mammalian enzyme chymosin, by co-transformation with pToC90. The construction of plasmid pToC56 is described in EP 98 993 A.

Transformants were selected for growth on minimal medium containing 10 mM acetamide, and screened for the presence of pToC56 by the ability to produce chymosin. A transformant was grown in shake flasks for 4 days at 30° C. in a medium containing maltodextrin, soybean meal and peptone. A transformant of pToC56 in *Aspergillus oryzae* IFO 4177 was grown together with the JaL121 transformant.

Each day, fermentation broth samples were collected and applied to SDS-Page and Western blotting. The blotting membrane was incubatecd with chymosin specific rabbit antibody, followed by goat rabbit antibody coupled to peroxidase.

Staining of the membrane showed that on the first and second day of fermentation, the supernatants from transformants of *Aspergillus oryzae* IFO 4177 contained small amounts of chymosin, or degradation products thereof. Later on no chymotrypsin was detected. In contrast, transformants of JaL121 contained at least ten times of full size chymosin. The amount of chymosin in the supernatants increased for the first two-three days and then remained constant.

I claim:

1. A method of producing a cell, comprising introducing a cloning vehicle into a parent filamentous fungal cell to form the cell whereby the cell produces a metalloprotease in an amount less than the parent cell, wherein the cell is capable of producing a heterologous protein.

2. The method of claim 1, wherein the parent cell is a wild-type cell.

3. The method of claim 1, wherein the heterologous protein is not native to the cell.

4. The method of claim 1, wherein the heterologous protein is native to the cell and the nucleic acid sequence encoding the native protein is operatively linked to a regulatory element required for expression of the native protein which is not native to the nucleic acid sequence.

5. The method of claim 1, wherein the heterologous protein is a lipolyliic enzyme.

6. The method of claim 1, wherein the heterologous protein is a proteolytic enzyme.

7. The method of claim 1, wherein the heterologous protein is an oxidoreductase.

8. The method of claim 1, wherein the cloning vehicle comprises a selectable marker.

9. The method of claim 1, wherein the cloning vehicle is introduced into the parent cell as an autonomously replicating plasmid or integrated into the chromosome.

10. The method of claim 1, wherein the cloning vehicle comprises one or more nucleic acid sequences encoding the heterologous protein is operably linked to one or more appropriate regulatory regions.

11. The method of claim 1, wherein the regulatory regions are a promoter, terminator, and a polyadenylation region.

12. The method of claim 1, wherein the promoter is obtained from a gene encoding an amylase, protease, lipase, cellulase, xylanase, oxidoreductase, pectinase, cutinase, or glycolytic enzyme.

13. The method of claim 1, wherein the promoter is the *Aspergillus oryzae* TAKA amylase, *Aspergillus niger* neutral α-amylase, *Aspergillus niger* acid stable α-amylase, *Aspergillus niger* or *Aspergillus awamsii* glucoamylase (gluA), *Aspergillus niger* acetamidase, *Aspergillus oryzae* alkaline protease, *Aspergillus oryzae* triose phosphatase isomerase, *Rhizopus meihei* aspartic proteinase, or *Rhizopus meihei* lipase promoter.

14. The method of claim 13, wherein the promoter is the *Aspergillus oryzae* TAKA-amylase or *Aspergillus awamsii* gluA promoter.

15. The method of claim 1, wherein the parent cell is selected from the group consisting of Acremonium, Aspergillus, Candida, Cocliobolus, Endothia, Fusarium, Humicola, Neurospora, Penicillium, Podospora, Pyricularia, Rhizomucor, Rhizopus, Thermomyces, and Trichoderma.

16. The method of claim 15, wherein the parent cell is an Aspergillus cell.

17. The method of claim 15, wherein the parent cell is a Fusarium cell.

18. The method of claim 15, wherein the parent cell is a Trichoderma cell.

19. The method of claim 15, wherein the parent cell is selected from the group consisting of *Aspergillus oryzae, Aspergillus niger, Aspergillus nidulans, Aspergillus awamori, Aspergillus phoenicis, Aspergillus japonicus, Aspergillus foetus, Fusarium graminearum, Fusarium oxysporum, Fusarium solani, Humicola grisea, Neurospora crassa, Penicillium chrysogenum, Rhizomucor meihei, Trichoderma reesei*, and *Trichoderma viride*.

20. The method of claim 19, wherein the parent cell is an *Aspergillus niger* or *Aspergillus oryzae* cell.

21. The method of claim 19, wherein the parent cell is a *Trichoderma reesei* or *Trichoderma viride* cell.

22. The method of claim 1, wherein the metalloprotease is a neutral metalloprotease, having optimal proteolytic activity in the range of about pH 6–8.

23. The method of claim 1, wherein the cell has been produced by genetically modifying the parent cell by specific or random mutagenesis, PCR generated mutagenesis, site specific DNA deletion, insertion and/or substitution, gene disruption or gene replacement techniques, anti-sense techniques, or a combination thereof.

24. A method of producing a heterologous protein, comprising (a) cultivating a filamentous fungal cell under conditions suitable for production of the heterologous protein, wherein the filamentous fungal cell (i) comprises a nucleic acid sequence encoding the heterologous protein and (ii) produces a metalloprotease in an amount less than a parent of the filamentous fungal cell; and (b) isolating the heterologous protein.

25. The method of claim 24, wherein the heterologous protein is not native to the cell.

26. The method of claim 24, wherein the heterologous protein is native to the cell and the nucleic acid sequence encoding the native protein is operatively linked to a regulatory element required for expression of the native protein which is not native to the nucleic acid sequence.

27. The method of claim 24, wherein the heterologous protein is a lipolytic enzyme.

28. The method of claim 24, wherein the heterologous protein is a proteolytic enzyme.

29. The method of claim 24, wherein the heterologous protein is an oxidoreductase.

30. The method of claim 25, wherein the parent is a wild-type cell.

31. The method of claim 25, wherein the parent is selected from the group consisting of Acremonium, Aspergillus, Candida, Cochliobolus, Endothia, Fusarium, Humicola, Neurospora, Penicillium, Podospora, Pyricularia, Rhizomucor, Rhizopus, Thermomyces, and Trichoderma.

32. The method of claim 31, wherein the parent is an Aspergillus cell.

33. The method of claim 31, wherein the parent is a Fusarium cell.

34. The method of claim 31, wherein the parent is a Trichoderma cell.

35. The method of claim 31, wherein the parent is selected from the group consisting of *Aspergillus oryzae, Aspergillus niger, Aspergillus nidulans, Aspergillus awamori, Aspergillus phoenicis, Aspergillus japonicus, Aspergillus foetus, Fusarium graminearum, Fusarium oxysporum, Fusarium solani, Humicola grisea, Neurospora crassa, Penicillium chrysogenum, Rhizomucor meihei, Trichoderma reesei*, and *Trichoderma viride*.

36. The method of claim 35, wherein the parent is an *Aspergillus niger* or *Aspergillus oryzae* cell.

37. The method of claim 35, wherein the parent is a *Trichoderma reesei* or *Trichoderma viride* cell.

38. The method of claim 24, wherein the heterologous protein is insulin, growth hormone, glucagon, somatostatin, interferon, PDGF, factor VII, factor VIII, urokinase, EPO, chymosin, tissue plasminogen activator, or serum albumin.

39. The method of claim 24, wherein the heterologous protein is of fungal origin.

40. The method of claim 24, wherein the heterologous protein is a bacterial protein.

* * * * *

UNITED STATES PATENT AND TRADEMARK OFFICE

CERTIFICATE OF CORRECTION

PATENT NO.      :   5,968,774

DATED           :   October 19, 1999

INVENTOR(S)     :   Jan Lehmbeck

It is certified that error appears in the above-identified patent and that said Letters Patent is hereby corrected as shown below:

IN THE CLAIMS:

Column 25, line 50: delete "lipolyliic", insert --lipolytic--

Column 27, line 34: delete "25", insert --24--

Column 28, line 1: delete "25", insert --24--

Signed and Sealed this

Sixth Day of February, 2001

*Attest:*

*Attesting Officer*

Q. TODD DICKINSON

*Director of Patents and Trademarks*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 2052 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
ATGCGTTTCT CCGACTCTCT CCTCCTCATC GGCCTATCCA GCCTCGCTGG TGCTCATCCC      60

AGCAGAAGGG CTCCTAATCC TTCACCGCTG AGCAAGCGTG GCCTCGACCT GGAAGCTTTT     120

AAGCTTCCTC CCATGGCCGA GTACGTTCCT CAGGACGAGG TTCCTGATGA TGTCAGTGCC     180

AAGGTCGTCA CCAAGCGCGC TGATTACACC GAGACTGCCA AGGACTTGGT TAAGTCGACT     240

TTCCCCAAGG CTACTTTCCG TATGGTCACG GATCACTATG TTGGTAGCAA CGGAATTGCG     300

CATGTAAACT TTAAGCAGAC TGTCAACGGT ATTGATATCG ACAATGCTGA TTTCAACGTC     360

AACGTGGGTA TTCTCAAGAC TTTGGGGAGT TTGGAATGTG CTGACATGGA TACAGATTGG     420

CGCTGACGGC GAGGTCTTCT CCTACGGAAA CAGCTTCTAC GAGGGCAAGA TTCCCGGTCC     480

TCTTACCAAG CGTGACGAGA AAGACCCCGT CGACGCTCTC AAGGACACCG TTGATGTTCT     540

TTCTCTCCCC GTTGAGGCTG ACAAGGCCAA GGCTGAGAAG AAGAGCAAGA ACCACTACAC     600

CTTCACTGGT ACCAAGGGTA CCGTCAGCAA GCCCGAGGCT AAGCTCACCT ACCTTGTTGA     660

TGAGAACAAG GAGCTCAAGC TCACATGGAG AGTTGAGACT GATATTGTTG ACAACTGGCT     720

GTTGACTTAT GTCAATGCTG CCAAGACTGA TGAGGTTGTT GGTGTTGTTG ACTACGTCAA     780
```

```
TGAGGCGACA TACAAGGTCT AGTACGTATT TCCATAAATT GACGATTGGG AAAGAATTGA    840

CCGTTGTATT ATAGTCCTTG GGGTGTCAAT GATCCCTCCA AGGGATCTCG CTCCACTGTT    900

GAGAACCCCT GGAATCTCGC GGCCTCCGAG TTCACCTGGC TCAGCGACGG CTCAAACAAC    960

TACACCACAA CCCGCGGGAA CAATGGAATT GCACAGGTGA ATCCTTCAGG GGGCTCCACG   1020

TATCTGAACA ATTACCGTCC TGATAGCCCG TCGCTGAAGT TCGAGTATGA TTACTCCACC   1080

AGCACCACTA CACCCACCAC CTACCGCGAT GCTTCCATCG CTCAGCTTTT CTACACAGCC   1140

AACAAGTACC ACGACCTCCT CTACCTTCTT GGCTTTACCG AACAGGCTGG TAACTTCCAG   1200

ACCAACAACA ATGGCCAGGG TGGTGTAGGA AACGATATGG TTATCCTCAA CGCTCAGGAC   1260

GGAAGCGGCA CCAACAACGC CAACTTCGCT ACACCCGCTG ACGGTCAGCC CGGCCGCATG   1320

CGAATGTATC TCTGGACATA CAGCACACCC CAGCGTGACT GCAGTTTCGA CGCTGGCGTT   1380

GTTATCCACG AGTACACTCA CGGTCTCTCC AACCGTCTCA CAGGTGGCCC TGCCAACTCG   1440

GGTTGTCTTC CCGGTGGTGA ATCCGGTGGC ATGGGTGAGG GCTGGGGTGA CTTCATGGCT   1500

ACTGCCATTC ACATCCAATC CAAGGATACC CGCGCTAGCA ACAAGGTCAT GGGTGACTGG   1560

GTGTACAACA ACGCAGCTGG TATCCGAGCT TATCCTTACA GTACAAGCCT TACCACTAAC   1620

CCTTACACTT ACAAGAGTGT TAACAGTCTC AGTGGAGTCC ATGCTATTGG TACTTACTGG   1680

GCTACTGTTC TGTATGAGGT TATGTGGAAC CTCATCGACA AGCATGGGAA GAATGATGCG   1740

GATGAGCCCA AATTCAACAA CGGCGTTCCT ACAGATGGCA AATATCTTGC TATGAAGTTA   1800

GTAGTGGATG GCATGTCGCT GTAAGTTGTC CCTTGGATTT GTAGGAGTTC TTATCTAACG   1860

TTTAATAGGC AACCTTGCAA CCCCAACATG GTCCAGGCCC GAGACGCCAT CATCGACGCC   1920

GACACCGCTC TTACCAAGGG AGCTAACAAG TGCGAGATCT GGAAGGGCTT TGCCAAGCGT   1980

GGTCTTGGAA CTGGTGCCAA GTATAGTGCT TCCAGCCGTA CTGAGAGCTT TGCTCTTCCT   2040

TCTGGATGTT AA                                                       2052
```

(2) INFORMATION FOR SEQ ID NO: 2:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO: 2:

```
Ala Thr Tyr Lys Val Tyr Pro Trp Gly Val Asn Asp Pro Ser Lys Gly
1               5                   10                  15

Ser Arg Ser Thr Val Glu Asn Pro Trp Asn Leu Ala Ala Ser Glu Phe
            20                  25                  30

Thr Trp Leu Ser Asp Gly Ser Asn Asn Tyr Thr Thr Arg Gly Asn
        35                  40                  45

Asn Gly Ile Ala Gln Val Asn Pro Ser Gly Gly Ser Thr Tyr Leu Asn
    50                  55                  60

Asn Tyr Arg Pro Asp Ser Pro Ser Leu Lys Phe Glu Tyr Asp Tyr Ser
65                  70                  75                  80

Thr Ser Thr Thr Thr Pro Thr Thr Tyr Arg Asp Ala Ser Ile Ala Gln
                85                  90                  95

Leu Phe Tyr Thr Ala Asn Lys Tyr His Asp Leu Leu Tyr Leu Leu Gly
            100                 105                 110

Phe Thr Glu Gln Ala Gly Asn Phe Gln Thr Asn Asn Asn Gly Gln Gly
        115                 120                 125
```

```
Gly Val Gly Asn Asp Met Val Ile Leu Asn Ala Gln Asp Gly Ser Gly
        130                 135                 140

Thr Asn Asn Ala Asn Phe Ala Thr Pro Ala Asp Gly Gln Pro Gly Arg
145                 150                 155                 160

Met Arg Met Tyr Leu Trp Thr Tyr Ser Thr Pro Gln Arg Asp Cys Ser
                165                 170                 175

Phe Asp Ala Gly Val Val Ile His Glu Tyr Thr His Gly Leu Ser Asn
            180                 185                 190

Arg Leu Thr Gly Gly Pro Ala Asn Ser Gly Cys Leu Pro Gly Gly Glu
        195                 200                 205

Ser Gly Gly Met Gly Glu Gly Trp Gly Asp Phe Met Ala Thr Ala Ile
    210                 215                 220

His Ile Gln Ser Lys Asp Thr Arg Ala Ser Asn Lys Val Met Gly Asp
225                 230                 235                 240

Trp Val Tyr Asn Asn Ala Ala Gly Ile Arg Ala Tyr Pro Tyr Ser Thr
                245                 250                 255

Ser Leu Thr Thr Asn Pro Tyr Thr Tyr Lys Ser Val Asn Ser Leu Ser
            260                 265                 270

Gly Val His Ala Ile Gly Thr Tyr Trp Ala Thr Val Leu Tyr Glu Val
        275                 280                 285

Met Trp Asn Leu Ile Asp Lys His Gly Lys Asn Asp Ala Asp Glu Pro
290                 295                 300

Lys Phe Asn Asn Gly Val Pro Thr Asp Gly Lys Tyr Leu Ala Met Lys
305                 310                 315                 320

Leu Val Val Asp Gly Met Ser Leu Gln Pro Cys Asn Pro Asn Met Val
                325                 330                 335

Gln Ala Arg Asp Ala Ile Ile Asp Ala Asp Thr Ala Leu Thr Lys Gly
            340                 345                 350

Ala Asn Lys Cys Glu Ile Trp Lys Gly Phe Ala Lys Arg Gly Leu Gly
        355                 360                 365

Thr Gly Ala Lys Tyr Ser Ala Ser Ser Arg Thr Glu Ser Phe Ala Leu
    370                 375                 380

Pro Ser Gly Cys
385

(2) INFORMATION FOR SEQ ID NO: 3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Ala Thr Tyr Lys Val Tyr Pro Trp Gly Val Asn Asp Pro Ser
1               5                   10

(2) INFORMATION FOR SEQ ID NO: 4:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:
```

```
GCGTGGGGGA TGAATGACCC GACGGAGGGC CCTCGCACCG TCATCAGCGA TCCATGGGAT        60

TCGTCCGCAT CTGCGTTCAC CTGGATCAGT GACGGAGAAA ACAACTATAC CACAACTCGC       120

GGCAACAACG GTATCGCGCA GTCGAACCCT ACCGGTGGAT CGCAGTACTT GAAGAACTAC       180

CGGCCTGATA GCCCCGATTT GAAATTCCAA TACCCCTATT CGTTCAACGC CACACCCCCA       240

GAGTCCTATA TTGATGCGTC TATCACTCAG CTTTTCTACA CTGCCAACAC GTACCACGAT       300

CTACTCTACA CTCTGGGCTT CAACGAGGAG GCCGGTAATT CCAGTACGA TAACAATGGA        360

AAAGGAGGTG CTGGAAACGA CTACGTGATC CTCAATGCTC AGGACGGTTC TGGCACCAAT       420

AACGCCAACT TCGCTACGCC CCCGGATGGA CAGCCCGGCC GCATGCGCAT GTACATATGG       480

ACCGAGTCCC AGCCTTACCG TGACGGCTCC TTCGAGGCTG GTATTGTGAT TCACGAGTAT       540

ACTCACGGCC GTATGTATCC CTTATGAACC CCAAGTAAGG CAGTCTGAAC TAACACCACG       600

GCACACAGTC TCTAACCGGC TCACTGGAGG ACCCGCTAAC TCTCGCTGTT TGAATGTCCT       660

TGAATCCGGC GGAATGGGTG AAGGTTGGGG AGACTTCATG GCCACGGTAT TTCGGCTCAA       720

GGTCGGCGAT TCTCACTTCG ATCCTTT                                          747

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGAGGAAGAT CTCTCTGGTA CTCTTCGATC TC                                     32

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGAGGAGAAT TCAAGCTTCT TCTACATCAC AGTTTGAAAG C                           41

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

CTAGGATCCA AGGCATTTAT GCGTGTCACT ACTCTC                                 36

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

-continued (ii) MOLECULE TYPE: cDNA (xi) SEQUENCE DESCRIPTION: SEQ ID NO:8:

CTACTCGAGT TAGCACTTGA GCTCGATAGC        30

(2) INFORMATION FOR SEQ ID NO:9:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:9:

CCCTTCTTTC CAAACCG        17

(2) INFORMATION FOR SEQ ID NO:10:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:10:

GGGTGAGCCA CTGCCTC        17